United States Patent [19]

Hengartner et al.

[11] 4,193,850

[45] Mar. 18, 1980

[54] ALKANOYLOXYLATION OF BETA-IONONE

[75] Inventors: Urs Hengartner, Roseland; Gilbert Reymond, Clinton; Valdemar Toome, Nutley, all of N.J.

[73] Assignee: Hoffmann-La Roche Inc., Nutley, N.J.

[21] Appl. No.: 29,170

[22] Filed: Apr. 12, 1979

[51] Int. Cl.² .................. C25B 3/02; C07C 35/08
[52] U.S. Cl. .................... 204/79; 204/59 R; 204/72
[58] Field of Search ............... 204/59 R, 72, 79, 80

[56] References Cited

U.S. PATENT DOCUMENTS

| 3,248,312 | 4/1966 | Young | 204/80 |
| 3,448,021 | 6/1969 | Koehl | 204/72 |
| 3,448,022 | 6/1969 | Koehl | 204/78 |
| 4,024,032 | 5/1977 | Weinberg | 204/59 R |

FOREIGN PATENT DOCUMENTS 476387 12/1937 United Kingdom ............... 204/72

*Primary Examiner*—F.C. Edmundson
*Attorney, Agent, or Firm*—Jon S. Saxe; Bernard S. Leon; William H. Epstein

[57] ABSTRACT

A method for electrochemically alkanoyloxylation of beta-ionone to alkanoyloxy-beta-ionone, an intermediate for canthaxanthin.

7 Claims, No Drawings

ALKANOYLOXYLATION OF BETA-IONONE

BACKGROUND OF INVENTION AND CITATION OF PRIOR ART

U.S. Pat. No. 4,098,827, Rosenberger, hydroxy-beta-ionone

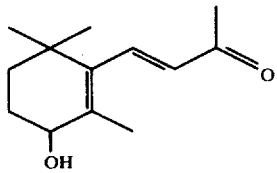
I a known intermediate for canthaxanthin has been produced from alpha-ionone via epoxidation and ring opening. While this is an efficient process, it is desired to produce the compound of formula I from a more readily available starting material than alpha-ionone such a beta-ionone.

In the past, monolefins have been acyloxylated electrochemically. See U.S. Pat. No. 3,448,022, Koehl Jr. June 3, 1969. While this process has been useful with monolefins such as cyclohexene, this process has not been applied to polyolefins let alone polyolefin containing an oxo substituent.

SUMMARY OF INVENTION

In accordance with this invention, it has been found that beta-ionone which has the formula:

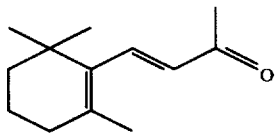
II can be electrochemically alkanoyloxylated by electrochemical mean to produce the compound of formula:

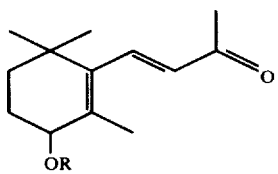
III wherein R is a lower alkanoyl.

The compound of formula III can be hydrolyzed by any suitable means to produce the compound of formula I. In accordance with this invention, it has been found that when a diolefin containing a keto group such as the compound of formula II is subjected to electrochemical alkanoyloxylation, alkanoyloxylation selectivity occurs within the cyclohex-1-ene ring at the 3-position in yields of at least 48%.

DETAILED DESCRIPTION

The term "lower alkanoyl" includes lower alkanoyl groups containing from 1 to 7 carbon atoms such as formyl acetyl, butyryl, hexanoyl, etc. The term "lower alkyl" designates saturated straight and branched chain aliphatic hydrocarbon groups containing from 1 to 7 carbon atoms such as methyl, ethyl, isopropyl, n-propyl, etc.

The electrochemical reaction of this invention is carried out in an electrochemical cell utilizing a solvent an an electrolyte; wherein the cell is divided by a semipermeable membrane and into the anodic and cathodic compartments. In carrying out this reaction, the compound of formula II is placed in the anodic compartment and the cell is subjected to an electrical potential. The reaction produces the compound of the formula III with a small amount of the compound of the formula:

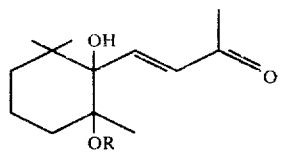
IV wherein R is as above as a byproduct in the anodic compartment of the cell.

In accordance with a preferred embodiment of this invention, it has been found that when the electrolyte comprises tetra (lower alkyl) ammonium-p-toluene sulfonate, more preferably tetra ethyl ammonium p-toluene sulfonate, the yield of the compound of formula III is substantially increased with a consequential reduction in the amount of the compound of formula IV.

In converting the compound of formula II to the compound of formula II in accordance with this invention, any conventionl method of electrolysis and any conventional electrolyte cell can be utilized. In carrying out this reaction, this reaction is carried out in the presence of a solvent and an electrolyte.

As the solvent medium for this reaction, the lower alkanoic acids are utilized. The particular lower alkanoic acid utilized depends upon the desired alkanoyl group R in the compound of formula III. Among the preferred alkanoic acid are acetic acid, 2-methylbutyric acid, proprionic acid, butanoic acid, and pentanoic acid. Generally, these acids are utilized in their anhydrous state. However, a small amount of water may be present. Generally, the solvent contains from about 0.5 to 5% by weight in water. However, this amount is not critical, since the acid can be utilized in the anhydrous state. On the other hand, substantial amounts of water may be used.

As an electrolyte, any conventional electrolyte common in electrolysis procedures can be utilized in accordance with this invention. Generally, the electrolyes utilized for this procedure are ammonium or alkali metal salts or cobalt salts of the acid used as a solvent. However, in accordance with the preferred embodiment of this invention, the preferred electrolye is tetra(-lower alkyl)ammonium-paratoluene sulfonate. The electrolyte is generally present in the solution in an amount of from about 0.5% to about 10% by weight of the lower alkanoic acid utilized as the solvent. In the preferred embodiment of this invention, the electrolyte itself contains about 40 weight percent to about 100% by weight of the tetra(lower alkyl)ammonium-paratoluene sulfonate with the remainder being a conventional electrolyte such as the alkali metal salts or quaternary ammonium salt of the lower alkanoic acid.

The electrodes may be of carbon or graphite or can be formed from any inert metal such as copper, palladium, stainless steel, platinum, silver, chromium, nickel, lead or gold. The cathode is preferably carbon, platinum, palladium, nickel, chromium or gold. In accordance with this invention, for best results it is preferred that the anode be carbon or graphite. Any conventional semipermeable membrane can be utilized to separate the anode and cathode compartments to prevent possible reaction of the products formed at one electrode with those of the others. Among the preferred semipermeable membrane materials are included procelain, fritted glass, polyethylene, etc. In carrying out the reaction, a potential of from about 5 to about 500 volts can be utilized from any conventional voltage source.

The current density may be maintained over a fairly wide range of from 0.001 to 5 and more preferably from 0.01 to 0.5 amp./sq.cm. As is known, the current density value determines the rate of speed of the electrolysis. In carrying out this reaction, temperature is not critical and this reaction can be carried out at room temperature. On the other hand, elevated and reduced temperatures can be utilized. Generally, it is preferred to carry out this reaction at a temperature of from 20° to 40° C. However, any temperature up to the boiling point of the solution can be utilized to carry out this reaction.

Depending upon the current density utilized, the reaction can take place in from 1 hour to 480 hours or longer. The compound of formula III which is produced by this reaction is produced in the anodic compartment. The compound of formula III can be recovered from the solution in the anodic compartment by conventional means such as extraction.

The compound of formula III can be converted to the compound of formula I by hydrolysis. Any conventional method of hydrolysis can be utilized to carry out this procedure.

The invention is further illustrated by the following examples. In the examples all of the reactions were carried out in a divided cell at current density of 0.0022 with a carbon rod as anode and a platinum wire as the cathode. In the examples, the electrolyte was either tetraethyl ammonium-p-toluenesulfonate (TEATS) or sodium acetate. The cell used in the Examples contained an anodic compartment and a cathodic compartment separated by fritted glass. The anodic compartment was a glass vessel 2½ in. in diameter, with a length of 3½ inches having a capacity of about 200 ml. The cathodic compartment was a glass tube connected through a standard joint to the vessel. The tube had a 1 inch diameter and length of 4 inches.

EXAMPLE 1

0.946 g of beta-ionone were subjected to anodic acetoxylation (0.3 M NaOc in AcOH, 2mA, 124 hrs). After this period, the reaction solution was partitioned between $CH_2Cl_2$ and water, the $CH_2Cl_2$ layer washed with water, sat. $NaHCO_3$ and brine and dried over $Na_2SO_4$. Concentration on a rotavap afforded 1.05 g of an oil. 996 mg of crude product were chromatographed on 150 g Silica Gel with $CHCl_3$—EtOAc 10:1 resp. 5:1. the following products were isolated and analyzed:

101 mg (11%) of beta-ionone
  390 mg (33%) of acetoxy-beta-ionone
  274 mg (22%) of compound IV, where R is acetyl, the analytical sample of IV where R is acetyl was prepared by evaporative distillation and crystallization from hexane: white needles, mp 84.5°–85.5°.

EXAMPLE 2

TEATS/AcOH Acetoxylation 0.932 g of beta-ionone were subjected to anodic acetoxylation (0.3 M TEATS in AcOH, 50 mA, 8.5 hr.). After this period, the brown reaction solution was concentrated on a rotavap to a volume of 10 ml and partitioned between $CH_2Cl_2$ and water. The $CH_2Cl_2$ layer was washed with sat. $NaHCO_3$ and brine, the aqueous phases reextracted with $CH_2Cl_2$ and the combined organic phases dried over $Na_2SO_4$. Concentration on a rotavap gave 1.23 g. of crude acetoxy-beta-ionone (GC-analysis: 53.5% pure). 1.18 g of this material was saponified at room temperature with sodium hydroxide in MeOH—$H_2O$ 20:3 v/v). After 1 hour, the reaction mixture was acidified with AcOH and concentrated on a rotavap. The residue was partitioned between toluene and water, the toluene layer washed with sat. aqueous $NaHCO_3$, the aqueous layers reextracted with toluene and the combined extracts dried ($Na_2SO_4$). Concentration at vacuo gave 826 mg of crude hydroxy-beta-ionone, which was evaporatively distilled (105°–120° C./0.1 mm) to give 597 mg (62%) of hydroxy-beta-ionone as a yellow viscous oil (GC-analysis 57.9% pure).

EXAMPLES 3–8

In Examples 3 through 8, 1 ml of 93% pure beta-ionone was subject to electrolyses by the method of Examples 1 and 2 utilizing the conditions in the following Table. In the Table, III designates Compound III where R is acetyl, IV designates Compound IV where R is acetyl and II designates unreacted beta-ionone. The yields given in the Tables were determined by vapor phase chromatography on the crude reaction mixture.

TABLE

Summary of Experimental Conditions

| Example | Electrolyte | Current | Time | % Yield[C] |
|---|---|---|---|---|
| 3 | 0.3 M NaOAc in glacial acetic acid | 2.2 mA | 153 hrs. | 60 III 28 IV 9 II |
| 4 | 0.3 M NaOAc in glacial acetic acid | 2.0 mA | 124 Hrs | 49 III 22 IV |
| 5 | 0.3 M NaOAc in 98% acetic acid | 5.0 mA | 52 hrs | 47 III 23 IV 18 II |
| 6 | 0.3 M NaOAc in glacial acetic acid | 2.0 mA | 216 hrs | 56 III 20 IV 5 II |
| 7 | 0.3 M TEATS in glacial acetic acid | 50.0 mA | 5 hrs 40 min | 65 III 24 II |
| 8 | 0.3 M TEATS in glacial acetic acid | 50.0 mA | 8 hrs 30 min | 54 III 18 II 28 (various unidentified by-products). |

I claim:

1. A process for producing alkanoyloxy beta-ionone of the formula:

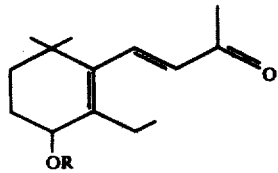

comprising electrolyzing a solution containing beta-ionone dissolved in a lower alkanoic acid in the presence of an electrolyte.

2. The process of claim 1 wherein said solution is electrolyzed in a cell containing a carbon anode.

3. The process of claim 2 wherein said electrolyte contains tetra(lower alkyl)ammonium toluene-p-sulfonate.

4. The process of claim 3 wherein said electrolyte contains (tetraethyl ammonium toluene p-sulfonate.

5. The process of claim 3 wherein said electrolyte is present in an amount of from 0.05 to 10% by weight of said solvent.

6. The process of claim 5 wherein said electrolyte contains at most 40% by weight of a alkali metal, ammonium, or cobalt salt of said lower alkanoic acid.

7. The process of claim 2 wherein said electrolysis is carried out at a current density of from 0.001 to 5 amp/sq cm.

* * * * *